(12) United States Patent
Donitzky et al.

(10) Patent No.: US 8,900,221 B2
(45) Date of Patent: Dec. 2, 2014

(54) APPARATUS FOR TREATING AN EYE WITH LASER RADIATION

(75) Inventors: Christof Donitzky, Eckental (DE); Olaf Kittelmann, Berlin (DE)

(73) Assignee: WaveLight GmbH, Erlangen (DE)

( * ) Notice: Subject to any disclaimer, the term of this patent is extended or adjusted under 35 U.S.C. 154(b) by 1229 days.

(21) Appl. No.: 12/416,795

(22) Filed: Apr. 1, 2009

(65) Prior Publication Data

US 2010/0256614 A1 Oct. 7, 2010

(51) Int. Cl.
*A61B 18/20* (2006.01)
*A61F 9/01* (2006.01)
*A61F 9/008* (2006.01)
*A61F 9/009* (2006.01)

(52) U.S. Cl.
CPC .......... *A61F 9/008* (2013.01); *A61F 9/00827* (2013.01); *A61F 2009/00872* (2013.01); *A61F 9/009* (2013.01); *A61F 9/00836* (2013.01)
USPC .......................................................... 606/4

(58) Field of Classification Search
USPC ........................................ 606/4, 5, 10, 11, 12
See application file for complete search history.

(56) References Cited

U.S. PATENT DOCUMENTS

| | | | | |
|---|---|---|---|---|
| 2001/0010003 A1* | 7/2001 | Lai | ................. | 606/107 |
| 2004/0044333 A1* | 3/2004 | Sugiura | ............. | 606/4 |
| 2006/0142742 A1* | 6/2006 | Donitzky | ............ | 606/5 |
| 2007/0055222 A1* | 3/2007 | Hohla et al. | ..... | 606/12 |
| 2007/0173795 A1* | 7/2007 | Frey et al. | .......... | 606/5 |
| 2008/0009840 A1* | 1/2008 | Chernyak | .......... | 606/5 |
| 2009/0069794 A1 | 3/2009 | Kurtz | | |
| 2010/0082017 A1* | 4/2010 | Zickler et al. | ..... | 606/4 |

FOREIGN PATENT DOCUMENTS

| | | |
|---|---|---|
| EP | 1844745 | 10/2007 |
| JP | 2012-522542 | 9/2012 |
| WO | WO2004/034917 | 4/2004 |
| WO | WO-2007/022993 | 3/2007 |
| WO | WO-2008/098381 | 8/2008 |
| WO | WO-2009/033111 | 3/2009 |
| WO | WO2009/036098 | 3/2009 |

OTHER PUBLICATIONS

European Patent Office, International Search Report dated Oct. 29, 2009 on Application No. PCT/EP2009/002383, 13 pages.
Japanese Patent Office, Translation of Office Action mailed Apr. 16, 2013 in JP 2012-522542, 3 pages.

\* cited by examiner

*Primary Examiner* — Ryan Severson
*Assistant Examiner* — Rachel S Papeika
(74) *Attorney, Agent, or Firm* — Haynes and Boone, LLP

(57) ABSTRACT

An apparatus for treating an eye with laser radiation exhibits the following: a laser radiation source (12) for generating laser radiation (14), means (20, 24, 40, 42, 44) for directing the laser radiation (14) onto the eye (10) for the purpose of an ophthalmological intervention on or in the eye, a controller (50) for controlling the laser radiation (14) in space and time in relation to the eye (10) in accordance with a treatment program (52) which is oriented towards a center (Z) of the eye, a camera (46) which records a feature of the eye (10), and an image-processing unit (50*a*) which derives information about the center (Z) of the eye (10) from the recording of the camera and enters this information into the controller (50), as a result of which the controller (50) controls the laser radiation (14, 14') in accordance with the treatment program and in a manner depending on the center of the eye derived in step e).

10 Claims, 2 Drawing Sheets

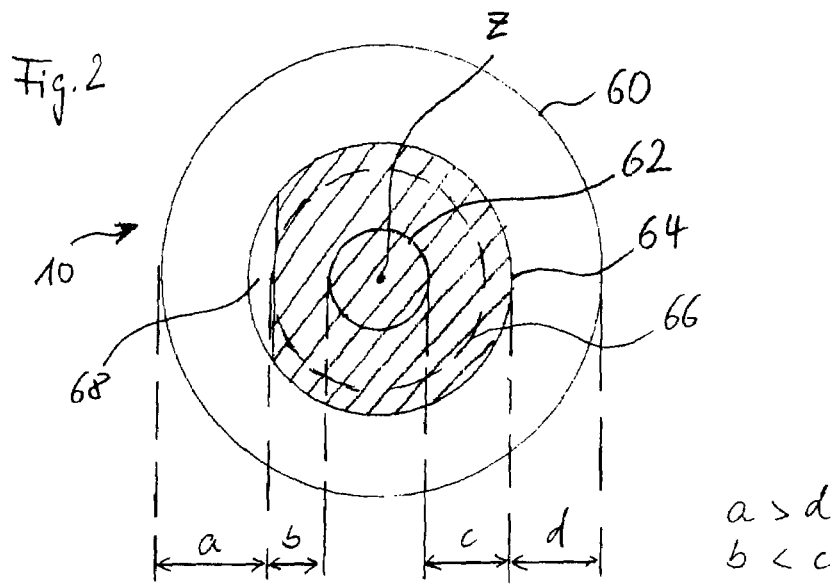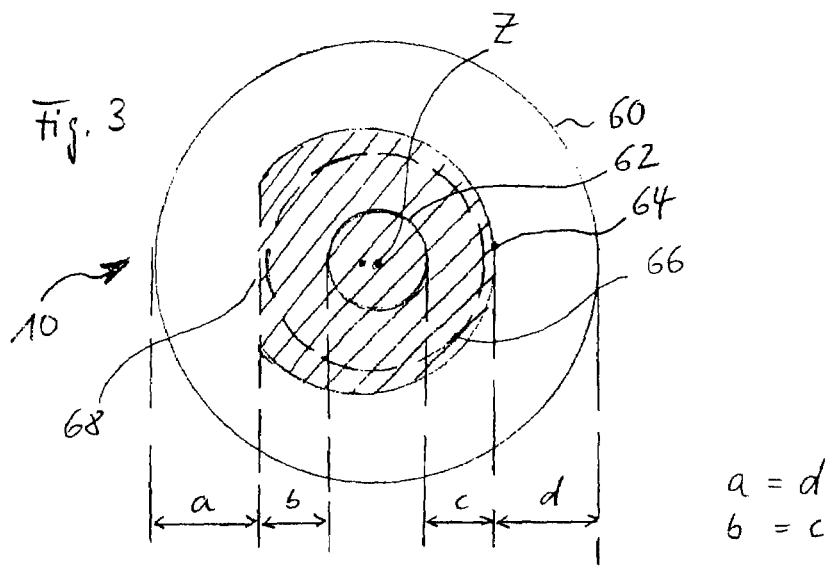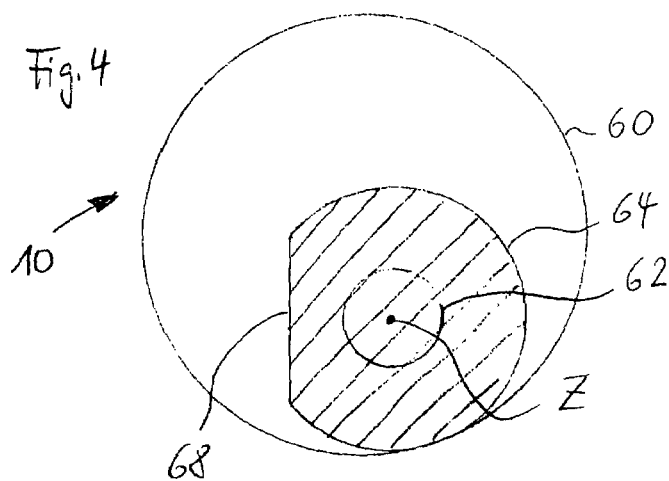

APPARATUS FOR TREATING AN EYE WITH LASER RADIATION

Figure 1:
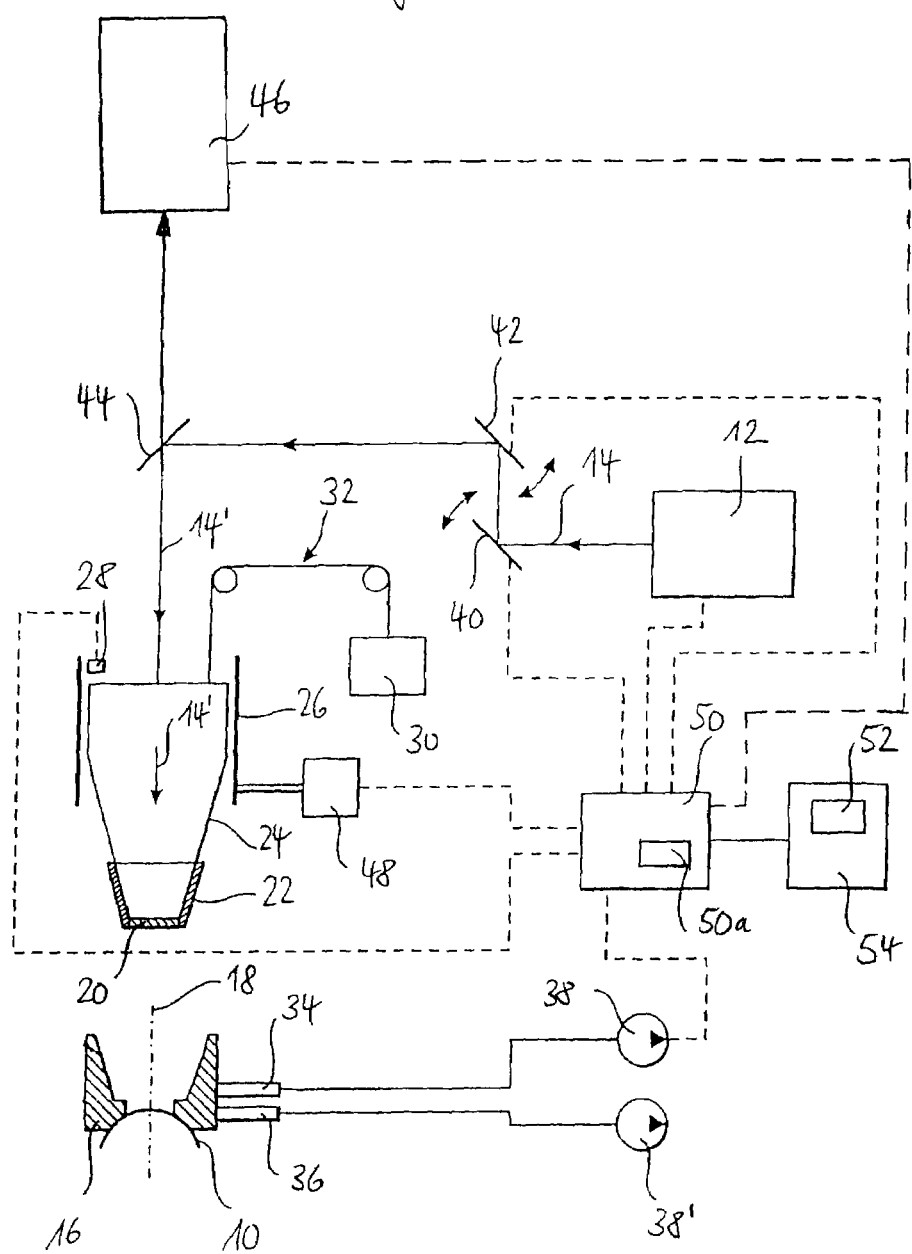

The invention relates to an apparatus for treating an eye with laser radiation.

In refractive ophthalmological surgery the refractive properties and imaging properties of the eye are changed by interventions in respect of the eye of a patient for the purpose of correcting or alleviating sight defects. Known, in particular, is the LASIK process, wherein the cornea of the eye is reshaped. In the conventional LASIK process, in a first step a flat corneal incision is made with a mechanical microkeratome, in order in this way to produce a so-called flap which remains firmly connected to the cornea on one side, so that it can be folded upwards in order to expose underlying corneal tissue (stroma). In the exposed stroma the so-called ablation—that is to say, the removal of tissue by means of, ordinarily, excimer-laser radiation—is then carried out, whereupon the flap is then folded back and heals up. In this process the epithelium remains largely uninjured and the healing process takes place relatively quickly and in pain-free manner. In a conventional mechanical microkeratome a sharp blade oscillates.

For the purpose of cutting the flap, the mechanical microkeratome has recently been increasingly replaced by laser radiation. The laser radiation is focused below the surface of the cornea and guided on a trajectory, the power densities being so high that a continuous incision arises by virtue of photodisruptive effects. In order to obtain the high power densities, extremely short laser pulses within the femtosecond range are employed, for which reason this process is also designated as fs LASIK. The present invention relates, in particular, to this fs LASIK but, above and beyond this, also to any other process for treating an eye with laser radiation, wherein the radiation is also guided in space and time in relation to the eye in accordance with a so-called treatment program. It will be understood that this control of the laser radiation in space and time has to be effected in relation to a precisely defined and reproducible reference-point of the eye. By way of such a reference-point, as a general rule a so-called centre of the eye is chosen—that is to say, a point situated centrally—which serves as reference for the local guidance of the laser radiation over the eye. Since, in the processes under discussion here, as a general rule the laser radiation is focused to small spots, the locations of each spot are accordingly aligned in relation to the stated centre as reference-point. The present invention relates, in particular, to fs LASIK but also to other eye treatments in which laser radiation has to be positioned in precisely defined manner in relation to the eye, such as, for instance, in the case of keratoplasty (e.g. anterior or posterior lamellar keratoplasty, perforating keratoplasty in the case of corneal transplants), fs lenticle extraction for the purpose of refractive correction, the cutting of intercorneal annular segments for the purpose of stabilising keratoconus and projection of the cornea, cataract incisions, presbyopia incision in the crystalline lens, intrastromal inlays, keratomy in the case of astigmatism, corneal resection etc.

In the state of the art, the centring of the surgical treatment location is ordinarily effected by adjustment of the so-called applicator, such as a suction ring, which on one side is connected to the eye by suction and on the other side exhibits a socket onto which focusing optics are capable of being coupled, with which the laser radiation is focused onto or into the cornea. In this process the surgeon performs the positioning of the applicator (suction ring) on the eye 'by eye', where appropriate utilising optical magnifying devices. The surgeon tries to place the applicator as centrically as possible in relation to certain contours of the eye. The guiding-point for this centring by eye may be, for example, the pupil or the iris. However, in this state of the art the optimal positioning and centring of the applicator, and hence of the surgical treatment location, relative to the eye depends greatly on the subjective capabilities of the surgeon. In other words: suboptimal conditions may arise in the course of this conventional positioning of the applicator.

The object underlying the invention is to make available an apparatus for treating an eye with laser radiation, wherein the radiation is controlled in space and time in relation to the eye in accordance with a treatment program in such a manner that a precise and reliably reproducible reference-point is available for the control of the laser radiation.

An apparatus according to the invention for achieving this object exhibits the following:

A laser radiation source for generating laser radiation, means for directing the laser radiation onto the eye for the purpose of an ophthalmological intervention on or in the eye, a controller for controlling the laser radiation in space and time in relation to the eye in accordance with a treatment program which is oriented towards a centre of the eye, a camera which records a feature of the eye, and an image-processing unit which derives information about the centre of the eye from the recording of the camera and enters this information into the controller, as a result of which the controller controls the laser radiation in accordance with the treatment program and in a manner depending on the derived centre of the eye.

Hence the invention enables an exact centring of the surgical treatment in relation to the target tissue (cornea). For this purpose a camera system is employed which on the basis of an eye feature—i.e. a specified anatomical structure of the eye—automatically recognises the treatment location by means of image processing—i.e. without influence of subjective influences having their origin in the respective surgeon. Suitable features for image processing for the purpose of ascertaining a reference-point, in particular a centre for the treatment, are geometrical structures of the eye from which a centre can be derived (ascertained) automatically by image processing, such as, for example, the pupil, the middle of which can be defined as centre, the iris structure or even the limbal structure. Alternatively or in addition, in the rear portion of the eye the structure of the retina can also be registered, and assertions concerning a reference-point for the laser treatment can be derived from the arrangement of blood vessels in the retinal region and/or from the orientation of the fovea relative to the pupil.

A special configuration of the invention has reference to the applicator introduced above—that is to say, for example, a suction ring. Such suction-ring techniques are described, for example, in U.S. Pat. No. 5,549,632, WO 03/002008 A1 and PCT/EP2008/006962. If the invention is employed together with an applicator, the camera is set up to record the applicator and at least one geometrical/structural feature of the eye, whereupon from this recording relating to both the applicator and the structure of the eye the image-processing unit derives a local relationship between the position of the applicator in relation to the eye and emits a corresponding signal to the laser controller, whereupon the controller then controls the laser radiation in relation to the eye in a manner depending on this signal. This means that a possible suboptimal positioning of the applicator in relation to the eye is compensated by computation in the course of control of the laser radiation—that is to say, for example, when the control program for the control of the laser radiation in accordance with a certain treatment program is firstly oriented towards the centre of the applicator but by virtue of the image processing it is established that the applicator is not optimally positioned centrically in relation to the eye, subsequently the treatment program is no longer oriented towards the centre of the applicator but rather towards the centre of the eye actually ascertained by the image processing.

Alternatively, in accordance with the invention the camera with the image-processing program can also be employed in such a way that when the middle of the applicator does not coincide ideally with the desired reference-point for the laser treatment (that is to say, for example, with the centre of the pupil), assistance is given to the surgeon as to how the applicator is best repositioned on the eye in such a way that the reference-point comes to be situated on the central axis of the applicator. Then the surgeon can firstly detach the applicator and then reattach it in accordance with this datum. In a fully mechanised system, this detachment and reattachment of the applicator may also occur in fully mechanical manner.

The invention is particularly suited for use in the case of the fs LASIK elucidated above for cutting the flap in such a manner that the geometry and positioning of the flap incision are precisely aligned with a reference-point on the eye in such a way that after the flap has been folded upwards a region of the stroma is available that is as large as possible and optimally situated in order to carry out the desired ablation.

Exemplary embodiments of the invention will be elucidated in more detail in the following on the basis of the drawing. Shown are:

FIG. 1 schematically, an exemplary embodiment of an apparatus for treating an eye with laser radiation;

FIG. 2 schematically, the top view of an eye and the positioning of a flap incision for fs LASIK;

FIG. 3 a schematic view corresponding to FIG. 2, wherein the flap incision is optimally positioned; and FIG. 4 another situation with optimised flap incision.

In FIG. 1 the eye to be treated with laser radiation is represented schematically by reference symbol 10. In this exemplary embodiment a laser 12 serves for the generation of femtosecond pulses. The laser radiation 14 is directed towards the eye 10 via means described in more detail further below.

With a suction ring 16, known as such, the eye is fixed, and on the central axis 18 of the suction ring 16 an applanation lens 20 is introduced into a socket of the suction ring—i.e. lowered downward from the position shown in FIG. 1. In the process, an interface unit 22 couples focusing optics 24 onto the suction ring 16. The focusing optics 24 are guided in a mount 26. Guidance is effected by means of a location sensor 28, the focusing optics 24 being suspended in feely floating manner via a counterweight 30 and a rope/pulley arrangement or a swivel joint, in order to enable a coupling of the interface unit with the focusing optics 24 onto the eye 10 in a manner that places virtually no burden on the eye.

The suction ring 16 is fixed by means of pipe connections 34, 36, known as such, and vacuum pumps 38.

The laser radiation 14 generated by the laser 12 is directed into the focusing optics 24 via mirrors 40, 42, 44 which are known as such. A computer controller 50 controls all the controllable components of the system, the control connections being indicated in FIG. 1 by dashed lines. In a memory 54 a control program is stored—i.e. a treatment program for the control of the laser radiation 14' in space and time in relation to the eye 10.

A camera 46 is arranged above a mirror 44 which is transmitting in respect of radiation coming from the eye 10, so that geometrical structures on the eye 10 can be recorded digitally with the camera 46, for example a CCD/CMOS camera. In the computer controller 50 an image-processing unit 50a is located which processes images supplied by the camera 46, in order to derive from a specified geometrical structure of the eye—such as the pupil, for example—a reference-point, in particular a centre, in accordance with which the controller 50 executes the treatment program 52. The arrangement according to FIG. 1 is elucidated in more detail in international patent application PCT/EP2008/006962, which is included here in full by reference.

FIGS. 2, 3 and 4 show schematically, in a top view of an eye 10, details of the image processing with the camera 46 and with the image-processing unit 50a.

FIGS. 2, 3 and 4 show schematically the periphery 60 of the optically useful surface of the cornea. The pupil is marked by reference symbol 62. 64 denotes the periphery of a possible flap incision—that is to say, the hatched region in the Figures.

Reference symbol 66 marks with a dashed line the ablation region—that is to say, that region of the cornea in which corneal tissue in the stroma is to be ablated after the flap has been folded back (according to the periphery 64). As described in the introduction, the flap has a region of connection to the cornea that is not cut, ordinarily designated as a hinge, this being marked in the Figures by reference symbol 68.

According to FIG. 2, the pupil 62 has a centre Z. The hinge region 68 for the flap cannot be used for the laser ablation, so that with concentric arrangement of the flap periphery 64 in relation to the pupil 62 a suboptimal region for the ablation arises. By virtue of the hinge 68, distance a according to FIG. 2 is greater than distance d on the side of the cornea situated opposite the hinge 68. The spacing b between the hinge 68 and the pupil 62 on the hinge side is also smaller than the corresponding spacing c on the opposite side, as is indicated in FIG. 2.

In the exemplary embodiment that is represented, the camera 46 records the pupil 62 and derives from this feature the position of the centre Z of the pupil in accordance with an algorithm that is known as such, for instance in a manner analogous to a so-called centre-of-gravity derivation in the case of a pupil shape that is not totally circular. The image-processing unit 50a in the control computer 50 now processes the recording of the image in such a way that a maximal ablation zone 66 is obtained, in that, according to FIG. 3, spacing a defined therein becomes equal to spacing d, and analogously spacing b becomes equal to spacing c, these spacings, as represented graphically, always being measured perpendicular to the edge of the hinge 68. Consequently a flap periphery 64 arises which is not precisely centric in relation to the pupillary centre Z. Accordingly, for the purpose of obtaining a maximal ablation zone the periphery 64 for the flap incision is offset in relation to the pupillary centre Z, and with the aid of the camera 46 and the image-processing unit 50a the treatment program for controlling the laser radiation 14 for producing the flap incision is automatically offset geometrically in relation to the reference-point Z in such a way that the spacings a, b, c, d that are drawn in FIG. 3 at least approximately satisfy the stated equality relations.

FIG. 4 shows schematically a somewhat extreme situation in the case of a patient's eye with greatly offset pupil 62 in relation to the midpoint of the optically useful surface 60. Also in this exemplary embodiment the flap periphery 64 is not chosen to be concentric in relation to the pupillary centre Z, but rather the centre of the flap periphery 64 is offset in relation to the centre Z of the pupil in a direction perpendicular to the edge of the hinge 68, whereby a restriction obtains with respect to the maximum possible diameter of the flap by virtue of the fact that the diameter of the flap can only be produced within the optically useful surface 60.

The exemplary embodiments show an objective, i.e. automated, positioning of the ablation region 66.

The invention claimed is:

1. Apparatus for treating an eye with laser radiation, exhibiting the following:
   a laser radiation source for generating laser radiation,
   focusing optics for directing the laser radiation onto the eye for the purpose of an ophthalmological intervention on or in the eye, the ophthalmological intervention including cutting a flap in a cornea of the eye such that when the flap is folded upwards a region of a stroma is exposed for ablation,
   a computer controller for controlling the laser radiation in space and time in relation to the eye in order to cut the flap in accordance with a treatment program which is oriented towards a centre of the eye,
   a suction ring configured to be fixedly coupled to the eye and the focusing optics,
   a camera which records a pupil of the eye and at least a portion of the suction ring, and
   an image-processing unit in communication with the camera and the computer controller, wherein the image-processing unit derives information about the centre of the eye from a position of a center of the pupil from the recording of the camera and a local relationship between the position of the suction ring and the center of the pupil of the eye from the recording of the camera, the image-processing unit enters this information into the computer controller, wherein the computer controller controls the laser radiation in accordance with the treatment program to cut the flap in a manner depending on the centre of the eye and the local relationship between the position of the suction ring and the center of the pupil of the eye as derived by the image-processing unit such that a periphery of the flap is offset in relation to the center of the pupil.

2. Apparatus according to claim 1, characterised in that the laser radiation source generates femtosecond pulses.

3. Apparatus according to claim 1, characterised in that the image-processing unit derives a centre for the ophthalmological intervention from the recorded pupil of the eye and the treatment program is oriented towards this centre.

4. Apparatus according to claim 1, characterised in that in the course of the control of the laser radiation the controller compensates for an offset of a midpoint of the suction ring from a midpoint of the eye.

5. An apparatus for treating an eye with laser radiation, comprising:
   a laser radiation source for generating a pulsed laser beam;
   focusing optics for directing the pulsed laser beam onto the eye for the purpose of making a flap incision in a cornea;
   a suction ring configured to be fixedly coupled to the eye and the focusing optics;
   a camera configured to record a pupil of the eye and at least a portion of the suction ring; and
   a computer controller in communication with the laser radiation source, focusing optics, and camera, the computer controller including an image-processing unit that determines a center of the eye from information regarding the pupil of the eye obtained from the camera and calculates a relationship between a position of the suction ring and the center of the eye, wherein the computer controller controls application of the pulsed laser beam onto the eye in accordance with a treatment program based on the center of the eye as determined by the image-processing unit and the relationship between the position of the suction ring and the center of the eye as determined by the image-processing unit such that a periphery of the flap is offset in relation to the center of the eye as determined by the image-processing unit in order to obtain a maximal ablation zone when the flap is folded upward to expose a region of a stroma.

6. The apparatus of claim 5, wherein lateral spacing between the periphery of the flap incision and a periphery of an optically useful surface of the cornea is symmetrical.

7. The apparatus of claim 6, wherein lateral spacing between a periphery of the maximal ablation zone of the exposed region of the stroma and a center of the pupil of the eye is symmetrical.

8. The apparatus of claim 6, wherein lateral spacing between a periphery of the maximal ablation zone of the exposed region of the stroma and a center of the pupil of the eye is asymmetrical.

9. The apparatus of claim 8, wherein the center of the pupil of the eye is calculated based on the pupil of the eye recorded by the camera.

10. The apparatus of claim 5, wherein the computer controller controls application of the pulsed laser beam onto the eye in a manner offset from a center of the suction ring.

* * * * *